United States Patent
Scholl et al.

(10) Patent No.: US 7,109,038 B2
(45) Date of Patent: Sep. 19, 2006

(54) OCCULT BLOOD DETECTION IN BIOLOGICAL SAMPLES BY LASER DESORPTION AND MATRIX-ASSISTED LASER DESORPTION/IONIZATION MASS SPECTROMETRY FOR BIOMEDICAL APPLICATIONS

(75) Inventors: Peter F. Scholl, Silver Spring, MD (US); Plamen Demirev, Ellicott City, MD (US); Andrew B. Feldman, Colulmbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/456,116

(22) Filed: Jun. 6, 2003

(65) Prior Publication Data

US 2003/0232446 A1    Dec. 18, 2003

Related U.S. Application Data

(60) Provisional application No. 60/388,566, filed on Jun. 13, 2002.

(51) Int. Cl.
*G01N 33/72* (2006.01)
*G01N 33/00* (2006.01)
*G01N 24/00* (2006.01)

(52) U.S. Cl. .................. 436/66; 436/63; 436/171; 436/173; 436/97; 356/300; 356/326; 250/281; 250/282

(58) Field of Classification Search .............. 436/63, 436/66, 64, 164, 171, 173, 97; 356/300, 356/326; 422/82.05; 250/281, 282, 287
See application file for complete search history.

(56) References Cited

U.S. PATENT DOCUMENTS

| | | | | |
|---|---|---|---|---|
| 3,980,437 A | * | 9/1976 | Kishimoto et al. | 422/55 |
| 4,038,031 A | * | 7/1977 | Lam | 436/97 |
| 4,219,336 A | * | 8/1980 | Guthlein et al. | 436/66 |
| 4,225,557 A | * | 9/1980 | Hartl et al. | 422/56 |
| 4,260,393 A | * | 4/1981 | Gibson | 436/66 |
| 4,468,468 A | * | 8/1984 | Benninghoven et al. | 436/173 |
| 4,937,197 A | * | 6/1990 | Lawrence | 436/66 |
| 4,988,628 A | * | 1/1991 | Nanji | 436/173 |
| 5,877,863 A | * | 3/1999 | Ross et al. | 346/445 |
| 6,528,320 B1 | * | 3/2003 | Hutchens et al. | 436/173 |
| 2005/0042698 A1 | * | 2/2005 | Demirev et al. | 435/7.22 |

OTHER PUBLICATIONS

Ausio et al. Analytical Chemistry, vol. 72, 2000, pp. 4874-4877.*
Luo et al. Biomedical Chromatography, vol. 9, 1995, pp. 113-122.*

* cited by examiner

*Primary Examiner*—Maureen M. Wallenhorst
(74) *Attorney, Agent, or Firm*—Francis A. Cooch

(57) ABSTRACT

Methods are described for detecting and quantifying occult blood in a biological sample using laser desorption mass spectrometry (LD MS). Biological samples that can be analyzed using various embodiments of the present invention include stool (fecal occult blood, FOB), and any bodily fluid including urine, cerebrospinal fluid and other bodily fluids. If the heme or heme metabolite is bound to protein, the sample is treated with acid before analysis to release the porphyrin. Some of the methods use LD MS with a time of flight analyzer (TOF) to detect and measure unbound heme, other hemoglobin metabolites and other molecules that have a porphyrin-based structure, e.g., bilirubin, biliverdin, protoporphyrin IX, and Zinc protoporphyrin in the biological sample. In other methods, matrix-assisted laser desorption/ionization mass spectrometry (MALDI MS) is used to detect and quantify the individual α- and β-polypeptide chains of hemoglobin.

8 Claims, 5 Drawing Sheets

LDMS detection of blood in stool only after treatment with formic acid: the heme LDMS signature is a unique biomarker for the presence of blood LD TOF mass spectra of protoporphyrin IX (PPIX) in stool
PPIX can be detected in stool from its mass spectrum MS for detection of occult blood in bodily fluids
HEME IS DETECTED IN FRESH URINE BY LD-TOF-MS

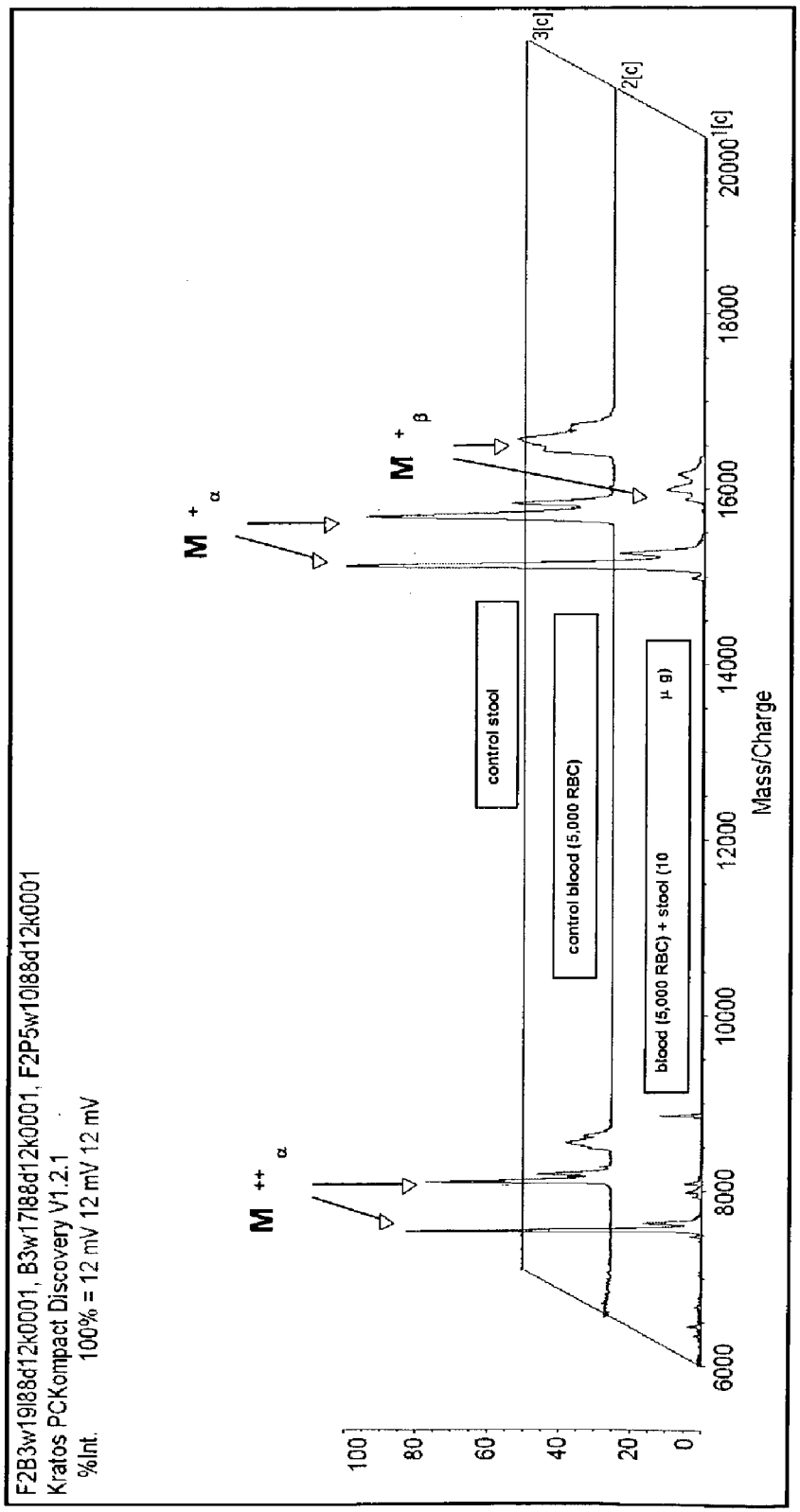

OCCULT BLOOD DETECTION IN BIOLOGICAL SAMPLES BY LASER DESORPTION AND MATRIX-ASSISTED LASER DESORPTION/IONIZATION MASS SPECTROMETRY FOR BIOMEDICAL APPLICATIONS

CROSS-REFERENCE TO RELATED APPLICATIONS

This application claims the benefit of prior U.S. provisional application No. 60/388,566 filed on Jun. 13, 2002, the entire contents of which are hereby incorporated by reference as if fully set forth herein under 35 U.S.C. Section 119(e). This application is also related to PCT International Application No. PCT/US03/09642, filed Mar. 28, 2003 (hereafter "Demirev"), the entire contents of which are hereby incorporated by reference.

BACKGROUND OF THE INVENTION

1. Field of the Invention

The methods of the present invention are in the field of blood detection using mass spectrometry, especially occult blood in feces (fecal occult blood test, FOB).

2. Description of the Related Art

Cancer is the second most common cause of death, behind cardiovascular disease. Apart from lung cancer in man and breast cancer in woman, intestinal cancer (carcinoma of the colon) is the second most common form of cancer in both sexes causing nearly one third of all malignancy-related deaths in North America. Cancers of the colon and rectum are sometimes referred to collectively as "colorectal cancer" (CRC). The situation is so serious that the American Cancer Society has recommended occult blood testing yearly for all individuals over 50 years of age, regardless of their medical history.

Most CRC cases begin with the development of benign polyps, finger-like growths that protrude into the intestinal cavity. Polyps can become cancerous, and they have the ability to invade normal colon tissue from which point the cancer spreads to other parts of the body (metastasizes). Among those over forty-five, 10% have colorectal polyps of which 1% will become malignant. Intestinal cancer generally develops very slowly and may remain undiagnosed for years, therefore, early detection of these lesions is critical to increase patient survival rates.

Colorectal cancers can usually be completely cured if the tumor is detected early. The initial symptoms are a change in customary bowel movements and gastrointestinal bleeding. Pain and weight loss only occur much later. The exact causes of colon and rectal cancers are not known, but risk appears to be associated with genetic, dietary, and lifestyle factors. Those with a personal or family history of colorectal cancer or polyps are at a higher risk, as are those with ulcerative colitis, inflammatory bowel disease, and immunodeficiency disorders. A rare inherited disease, called familial adenomatosis or polyposis, causes benign polyps to develop early in life and causes cancer in almost all affected persons unless the colon is removed. Risk also increases with age and with the occurrence of cancers in other parts of the body. High fat and meat diets are a risk factor, especially when combined with minimal fruit, vegetable, and fiber intake. Lifestyle factors include cigarette smoking, obesity, and a sedentary lifestyle.

The most-widely-used current method of colorectal cancer screening in the general population is searching for occult blood in the stool; these tests are called fecal occult blood tests (FOBT). FOBT include a number of different noninvasive tests that detect the presence of hidden (occult) blood in the stool. Occult blood may arise from any point along the digestive tract. Occult blood in stool is often the first, and in many cases the only, warning sign that a person has colorectal disease, including colon cancer. An easy, quick and cost-effective test for the detection of occult blood in stool can also help intestinal cancer detection at an early stage.

Because fecal occult blood (FOB) tests are most frequently used to screen patients for a hidden colonic malignancy before the patient exhibits symptoms, the consequences of missing any bleeding can be very serious. Conversely, FOB tests that are associated with a large number of false positives have consequences that are expensive and uncomfortable for the patient. Moreover, the possible complications of the additional follow-up tests involved are also considerable. FOB tests detect bleeding from almost anywhere along the length of the digestive tract. Therefore, many different diseases could cause a positive test result including colorectal cancer, esophagitis, gastritis, stomach cancer, ulcerative colitis and hemorrhoids. Follow up tests are typically required to identify the source of the occult blood.

The present chemical or immunochemical methods of FOB tests for colorectal cancer screening rely predominantly on the detection of heme or hemoglobin in feces. A well known chemical FOB test, HEMOCCULT™, is based on chemical reactions that detect the pseudoperoxidase property of heme by causing the catalysis of peroxide into oxygen and water, and the subsequent oxidation of a colorless dye into a colored form. HEMOCCULT II™ involves smearing a sample of stool onto guaiac-impregnated paper, which turns blue after treatment with hydrogen peroxide-containing developer if blood (heme) is present. Gum guaiac is the most commonly used color reagent. The HEMOCCULT™ test can detect levels of bleeding from the colon as low as 0.5 mg per day. FOB tests generate many false positives. Factors such as medications, multiple dietary constituents, delays in specimen handling, variability in fecal hydration, and storage of assay materials commonly confound results. A person ingesting peroxidase-containing food may exhibit a positive reaction (false positive). Analysis of one of the three randomized controlled studies assessing the value of HEMOCCULT™ suggests comparable mortality rates in screened and control populations.

Newer methods of detecting occult blood based on porphyrin (heme and protpoporphyrin IX) analysis or immunologic tests using anti-hemoglobin antibodies improve on these results. Immunochemical tests that use anti-hemoglobin antibodies specific for human blood in extracts from stool do not require dietary restrictions and they are highly specific, however, they are more complicated and expensive than peroxidase-based tests. Further, blood in the patient's stool sample may be altered by partial digestion so that the antibodies do not recognize hemoglobin, thereby generating a false negative.

An FOB test called HEMOQUANT™ is an FOBT based on a physical method. It uses optical fluorescence spectroscopy for the indirect measurement of heme. Since heme does not fluoresce (the iron ion quenches the fluorescence), the first step in that method is to release the iron atom from heme to obtain protoporphyrine IX (PPIX), which is a fluorescing molecule. The advantage of the HEMOQUANT™ test is that it is quantitative and relatively specific, but it is expensive and much more cumbersome than the usual screening tests. Like the HEMOCCULT™ test, the HEMOQUANT™ test is also affected by diet. In other tests, fecal occult blood is measured accurately by analyzing chromium levels in fecal samples collected for three to ten days; chromium is present in red blood cells. This test is used in cases where the exact amount of the blood loss is required and it is the only test that can accurately exclude blood loss from the gastrointestinal tract.

Because the available chemical and immunochemical FOB tests are plagued by false positive and/or false negative results, there is a need for a reliable, inexpensive FOB test that could also be used to detect occult blood in urine (hematuria).

1. Definitions

Biological sample means stool or feces, and any bodily fluid including tears, saliva, lavage fluids, cerebrospinal fluid, semen, and urine, and stool.

Bound heme means a molecule that is covalently or non-covalently bound to a polypeptide chain, e.g., one heme bound to each of the four subunits of hemoglobin (the oxygen-binding hemoglobin prosthetic group).

PPIX (protoporphyrin IX, $C_{34}H_{34}N_4O_4$) consists of a particular planar tetrapyrrole ring system.

Heme means ferriprotoporphyrin IX, $C_{34}H_{32}N_4O_4Fe$ that consists of a particular planar tetrapyrrole ring system that chelates iron.

Heme metabolites include but are not limited to biliverdin, bilirubin, and PPIX.

Unbound heme means free heme molecules, e.g. heme that is not bound to hemoglobin or other protein.

SUMMARY OF THE INVENTION

A method is disclosed using mass spectrometry for detecting blood in a biological sample from an animal where the sample is not whole blood and the method is based on detecting unbound heme in the sample. The method has the steps of: obtaining a biological sample that is not blood from the animal, preparing a test sample from the biological sample, depositing the test sample on a support, inserting the support into a mass spectrometer, obtaining a mass spectrum of the test sample, determining whether the mass spectrum shows a mass/charge signature of unbound heme, and if it is determined that the mass spectrum shows the mass/charge (m/z) signature of unbound heme, then concluding that the test sample contains blood.

In an embodiment of this aspect, the step b of preparing a test sample includes mixing the biological sample with an acid to form the test sample. In another embodiment of the method, the step c of depositing the test sample on a support, further includes the step of adding an acid to the deposited test sample. Any acid or mixture of acids can be used. In an embodiment of this aspect the acid is formic acid, trifluoroacetic acid, or mixtures thereof. In an embodiment of this aspect of using mass spectrometry to detect blood in a biological sample based on the presence of heme, the biological sample is feces making the method a FOBT. In other embodiments, the biological sample can be saliva, sputum, urine, semen, lavage fluid, cerebrospinal fluid or any other bodily fluid.

In another aspect of the invention a method for detecting porphyrin in a biological sample obtained from an animal using mass spectrometry is disclosed. The method has the steps of: obtaining a biological sample that is not blood from the animal, preparing a test sample from the biological sample, depositing the test sample on a support, inserting the support into a mass spectrometer, obtaining a mass spectrum of the test sample, determining whether the mass spectrum shows a mass/charge signature of porphyrin, and if it is determined that the mass spectrum shows the mass/charge signature of porphyrin, then concluding that the test sample contains porphyrin.

In an embodiment of this aspect, the step b of preparing a test sample includes mixing the biological sample with an acid to form the test sample. In another embodiment of the method, the step c of depositing the test sample on a support, further includes the step of adding an acid to the deposited test sample. Any acid or mixture of acids can be used. In an embodiment of this aspect the acid is formic acid, trifluoroacetic acid, hydrochloric acid, or mixtures thereof.

In an embodiment of the aspect of using mass spectrometry to detect blood in a biological sample based on the presence of porphyrin, the biological sample is feces making the method a FOBT. In other embodiments of this aspect, the biological sample is urine, semen, lavage fluid, cerebrospinal fluid, blood, or any other bodily fluid. Some embodiments of the method directed to the analysis of the porphyrin detect bilirubin, biliverdin, or protoporphyrin IX.

Some embodiments of each aspect of the above-described mass spectrometry methods permit the purification of the biological sample by adding to step b of preparing a test sample the steps of: suspending the biological sample in an acid to form a first suspension, centrifuging the first suspension to form a pellet, resuspending the pellet in a buffer to form a second suspension, and obtaining an aliquot of the second suspension to form a test sample.

In some embodiments of each aspect of the above-described mass spectrometry methods (that based on detecting unbound heme and that based on detecting other porphyrins), the mass spectrometer in step d is a laser desorption mass spectrometer that optionally has a time of flight mass analyzer. In another embodiment the mass spectrometer in step d includes at least one of an ultraviolet wavelength, a visible wavelength and an infrared wavelength laser directed onto the support.

In another aspect of the invention a method for detecting blood in a biological sample obtained from an animal using MALDI mass spectrometry is disclosed. The method has the steps of: obtaining a biological sample that is not blood from the animal, preparing a test sample from the biological sample, depositing the test sample on a support, inserting the support into a mass spectrometer, obtaining a mass spectrum of the test sample, determining whether the mass spectrum shows a mass/charge signature of hemoglobin polypeptide chains, and if it is determined that the mass spectrum shows the mass/charge signature of hemoglobin polypeptide chains, then concluding that the test sample contains porphyrin.

BRIEF DESCRIPTION OF THE DRAWINGS

Methods are described in part with reference to specific embodiments thereof. It will, however, be evident that various modifications and changes may be made to the inventions without departing from the broader spirit and scope of the invention.

FIG. 5 is a collection of matrix-assisted laserdesorption/ionization (MALDI) mass spectra showing the presence of singly and doubly charged ions formed from the alpha- and beta-polypeptide chains of hemoglobin.

DETAILED DESCRIPTION

Figure 1:
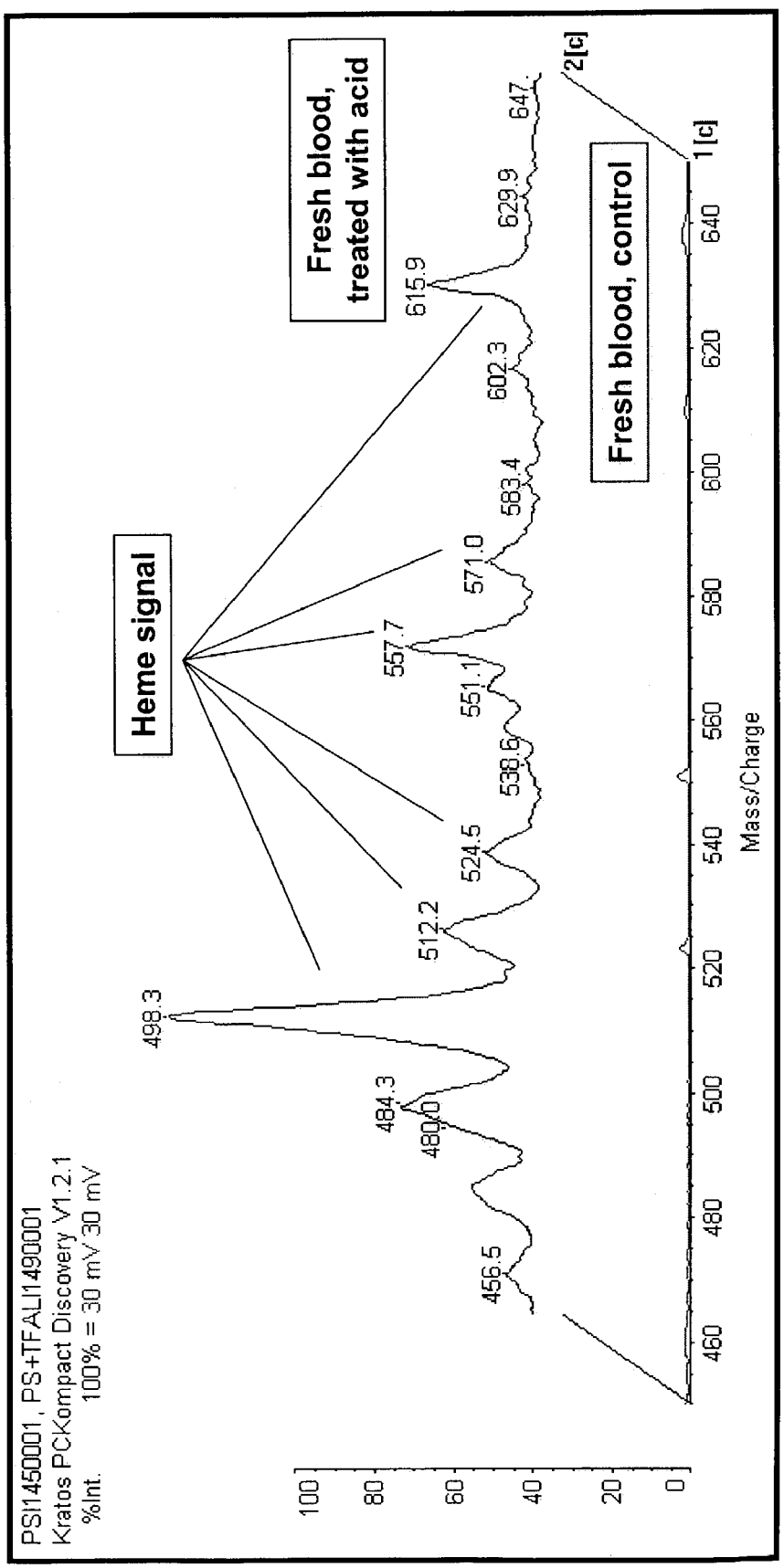
FIG. 1 is a collection of laser desorption (LD) mass spectra that show the presence of characteristic heme ion signals in whole blood treated with acid.

Methods using laser desorption mass spectrometry (LD MS) are described that directly detect and quantify occult blood in a biological sample. Biological samples that can be analyzed using various embodiments of the present invention include stool (fecal occult blood, FOB), urine, cerebrospinal fluid, lavage fluids, tears, saliva, sputum, and semen, among others. All of the illustrated embodiments of the present methods use LD MS with a time flight analyzer (TOF). A TOF analyzer is optional. In some embodiments, the presence of blood in a biological sample is determined by using LD MS to detect and measure heme and other porphyrins including protoporphyrin IX, bilirubin, biliverdin, and Zn protoporphyrin in a biological sample. Heme and some porphyrins exist in blood in a bound state, therefore in some embodiments, the biological sample is treated with or mixed with one or more acids to for unbound heme and unbound porphyrins. In some embodiments, matrix-assisted laser desorption/ionization mass spectrometry (MALDI MS) is used to detect and quantify the individual (α- and β-polypeptide chains of hemoglobin in a biological sample. LD MS analysis is a direct measurement of the unique mass spectral signature of these molecules. Therefore, the present methods are not plagued by false positive results that are common in other FOB tests such as indirect tests that measure heme based on its pseudoperoxidase-activity (HEMOCCULT™), or the HEMOQUANT™ test that measures the fluorescence of the heme metabolite PPIX.

In the following description, for the purposes of explanation, numerous specific details are set forth in order to provide a thorough understanding of the present invention. It will be apparent, however, to one skilled in the art that the present invention may be practiced without these specific details.

Heme and other porphyrins (such as PPIX) are abundant in normal whole blood samples, however, they do not exist in a free state. Heme and PPIX are bound or chelated by a variety of biomolecules such as hemoglobin, hemopexin and albumin. Complexed or bound heme is typically compartmentalized within specialized cells such as erythrocytes and hepatocytes (liver cells). Under normal physiologic conditions, the binding or complexing of heme and other porphyrins to various intracellular proteins prevents their direct detection by LD mass spectrometric analysis. Bound heme is itself mass spectrometrically "silent." The structure of PPIX is shown below; it is sometimes complexed with various metals including copper and zinc.

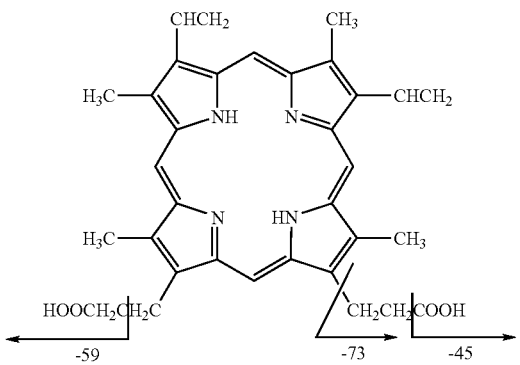

In the course of hemoglobin catabolism in the spleen, hemoglobin is converted to verdohemoglobin when the porphyrin ring is split and the open heme complexed with globin chains. Iron is then removed from heme and an open porphyrin ring form called biliverdin is formed. Biliverdin is reduced to bilirubin in the liver and is excreted in bile. It is important to be able to unambiguously detect and, in certain circumstances, quantify hemoglobin and its byproducts in feces and urine. There are some known correlations between the presence of hemoglobin and its metabolites in feces, and the site of origin of the fecal occult blood. For example, hemoglobin in the stomach is converted by hydrochloric acid to protoporphyrin IX (PPIX). Thus it is accepted that the presence of PPIX in stool signifies blood loss in the upper gastrointestinal (GI) tract. By contrast, detection of hemoglobin in stool focuses clinical attention toward diseases of the distal GI tract including colonic carcinoma or polyposis, hemorrhoids or rectal fissures. Other general correlations between FOB and diseases are listed in Table 1 below:

TABLE 1

| DISEASES INDICATED BY FECAL OCCULT BLOOD | |
| --- | --- |
| Bleeding esophageal varices | Esophagitis |
| Gastritis | GI (gastrointestinal) trauma |
| GI tumor | Hemorrhoids |
| Fissures | Inflammatory bowel disease |
| Colon polyp or colon cancer | Peptic ulcer |
| Complications of recent GI surgery | Angiodysplasia of the colon |
| Evaluation of anemia | Parasitic infections |
| Hepatitis | |

The HEMOQUANT™ test is based on an indirect measurement of heme by analyzing the fluorescing heme metabolite protoporphyrin IX (PPIX) using fluorescent spectroscopy, which is not similar to mass spectrometry. Because a certain amount of PPIX is formed in the upper intestines, false positive tests can be obtained unless additional steps are taken to distinguish between PPIX generated from heme and PPIX generated in the intestines. Both the HEMOCCULT™ and HEMOQUANT™ tests are indirect tests for heme. The first is based on chemical reactions that detect the pseudoperoxidase property of heme. Because PPIX does not contain iron, it cannot be detected using peroxidase-based FOB tests like HEMOCCULT™. HEMOCCULT™ will always miss PPIX and e.g. the alpha- and beta-hemoglobin polypeptide chains. Further, the HEMOCCULT™ and HEMOQUANT™ methods can only detect the presence of one compound at a time. By contrast, the embodiments of the methods of the present invention use mass spectrometry for the direct detection and quantitation of heme and heme metabolites (LD MS) and hemoglobin alpha- and beta-chains (MALDI MS).

MALDI MS has been used by others to detect and quantify various forms of hemoglobin in whole blood, for example, to identify different human hemoglobin variants in persons suffering from inborn genetic disorders, e.g., sickle-cell anemias based on the different molecular weights of normal vs. mutated hemoglobin variants. A. Shimizu, et al., Journal of Chromatography B, vol.776 (2002) 15–30; Urban et al., Clinical Chemistry vol. 48, No. 6, 2002 947–949; and C. Houston, et al., Rapid Communications in Mass Spectrometry, vol. 11, 1435–1439 (1997). These reports are limited to the use of MALDI MS to detect hemoglobin in whole blood.

Laser desorption mass spectrometry (LD MS) is known to be particularly well suited for the analysis of porphyrins such as PPIX and heme. Both infrared (IR) and ultraviolet (UV) laser desorption mass spectrometry have been applied for structural characterization of natural porphyrins and their metabolites, synthetic monomeric porphyrins (e.g., used in photodynamic therapy), porphyrin polymers and multimeric arrays. The porphyrin molecule can have different side chain groups, and contains a pi-electron conjugated system, which makes it an efficient photo-absorber in the visible and near ultraviolet range. This feature, combined with the low ionization potential of protoporphyrins, warrants that laser desorption mass spectrometry will possess extremely low detection limits for porphyrins. In Demirev we reported the use of mass spectrometry to detect the presence of malaria parasites in blood by the presence of unbound heme, which is not present in normal, uninfected blood. We showed that LD MS analysis of heme produced characteristic (heme "signature") fragment ions at a mass charge ratio (m/z) of 498, 512, 526, 557, 571, and a molecular ion at m/z 616. Demirev et al., Analytical Chemistry, vol. 74:2002, p.3262; and U.S. Provisional Application Nos. 60/368,234 and 60/388,597; the entire contents of which is hereby incorporated by reference as if fully set forth herein.

It has now been discovered that LD MS can be used to detect heme and other porphyrins in biological samples as defined herein. It has also been discovered that MALDI-MS can detect the alpha- and beta-chains of hemoglobin in biological samples. The present methods are therefore different from the earlier reports of the use of MALDI MS to detect hemoglobin in whole blood.

1.1 Analysis of Occult Blood Using LD MS

Mass spectrometry has been developed in recent years into a viable technique for medicine, molecular biology and biochemistry. Laser desorption (LD) time-of-flight (TOF) mass spectrometry, in particular, has enhanced the prospects for field-deployable, robust, automated, and miniaturized detection systems for applications in a variety of diagnostic areas—from microbiology to genetic diseases. The ultraviolet or visible light LD-TOF mass spectrometer is used in an illustrated embodiment. In other embodiments other mass spectral methods, including MALDI, may be used.

In general, mass spectrometry provides a means of "weighing" individual molecules by ionizing the molecules and transferring the ions in a vacuum. Under the influence of combinations of electric and magnetic fields, the ions follow trajectories depending on their individual mass (m) and charge (z). In the range of molecules with low molecular weight, mass spectrometry has long been part of the routine physical-organic repertoire for analysis and characterization of organic molecules by the determination of the mass of the parent molecular ion. In addition, by virtue of its excess internal energy, the molecular ion is fragmented, forming secondary ions. Such fragmentation pattern/pathways very often allow the derivation of detailed structural information. Many applications of mass spectrometric methods are known in the art, particularly in the field of bioscience, and are summarized in Methods of Enzymology, Vol. 193: "Mass Spectrometry" (J. A. McCloskey, editor), 1990, Academic Press, New York.

Although the LD-TOF mass spectrometer is used in some of the experiments illustrated in FIGS. 1–5, other mass spectrometers can also be used. For example, mass spectrometers that differ based on ionization after primary ion impact (secondary ion mass spectrometry—SIMS), and those that analyze the ion mass-to-charge ratio by other means such as ion cyclotron resonance (ICR) and Fourier Transform, or linear or 3-D trapping radiofrequency quadrupole instruments. For SIMS, the samples are typically bombarded by atomic or polyatomic ions with energies from thousands of electron volts (keV) to millions of electron volts (MeV). Secondary ions such as heme molecular ions and heme fragments are desorbed/sputtered and then mass analyzed by, e.g., a TOF or a double-focusing mass analyzer. Even more detailed information on the specific structure of the analyzed molecule can be obtained using a mass spectrometry/mass spectrometry (tandem) system, e.g., quadrupole-TOF configuration. This is useful for blood, heme or porphyrin detection under conditions of very high background in the m/z (mass-to-charge ratio) range where heme biomarker ions are detected.

Embodiments of the present method illustrated in FIGS. 1–4 use LD MS to detect heme or PPIX. Heme (and some other porphyrins like bilirubin) exist in a bound state in the biological samples, therefore in some experiments the samples were treated with acid to convert bound heme unbound heme for LD MS analysis. In some cases, the porphyrin molecules being analyzed may already exist in an unbound state in the samples.

LD MS of whole blood samples are illustrated in FIG. 1. The LD MS spectrum of the untreated fresh blood sample (bottom) does not show the presence of heme; the spectrum is almost completely flat in the m/z range from 420 to 640. By contrast, fresh blood treated with acid (trifluoracetic acid or TFA) displays the characteristic heme signature. For each experiment, 0.3 microliters of fresh blood was deposited on a support and dried. The control was run without further treatment. To form the test sample, 0.3 microliters of TFA was added to the dried blood on the support. The fresh blood sample treated with TFA was then dried, and the support was inserted into the LD-TOF mass spectrometer for heme analysis. As the top spectrum shows, the acid-treated test sample displays characteristic heme signals at m/z 497.9, 511.5, 525.7, 543.9, 557.8, 571.3, and 616.6. These results show that bound heme is "silent" under LD MS conditions, and that treatment with an acid permits the separation of heme from hemoglobin thereby enabling its detection. Any acid or combination of acids can be used to release heme from hemoglobin. The sample can be treated or mixed with an acid before or after it is deposited on a sample support. Any technique known in the art that releases heme from hemoglobin can be used. An embodiment of the present method is therefore directed to the detection of blood in a biological sample using LD MS detection of heme.

The results in FIG. 1 and in the experiments shown in FIG. 2 below show that no purification steps are required to detect heme in a biological sample. In any of the embodiments of the present invention, the amount of heme or porphyrin or hemoglobin polypeptide chains (described below) in a test sample can be quantified by calibration using an internal or an external standard using methods known in the art.

Figure 2:
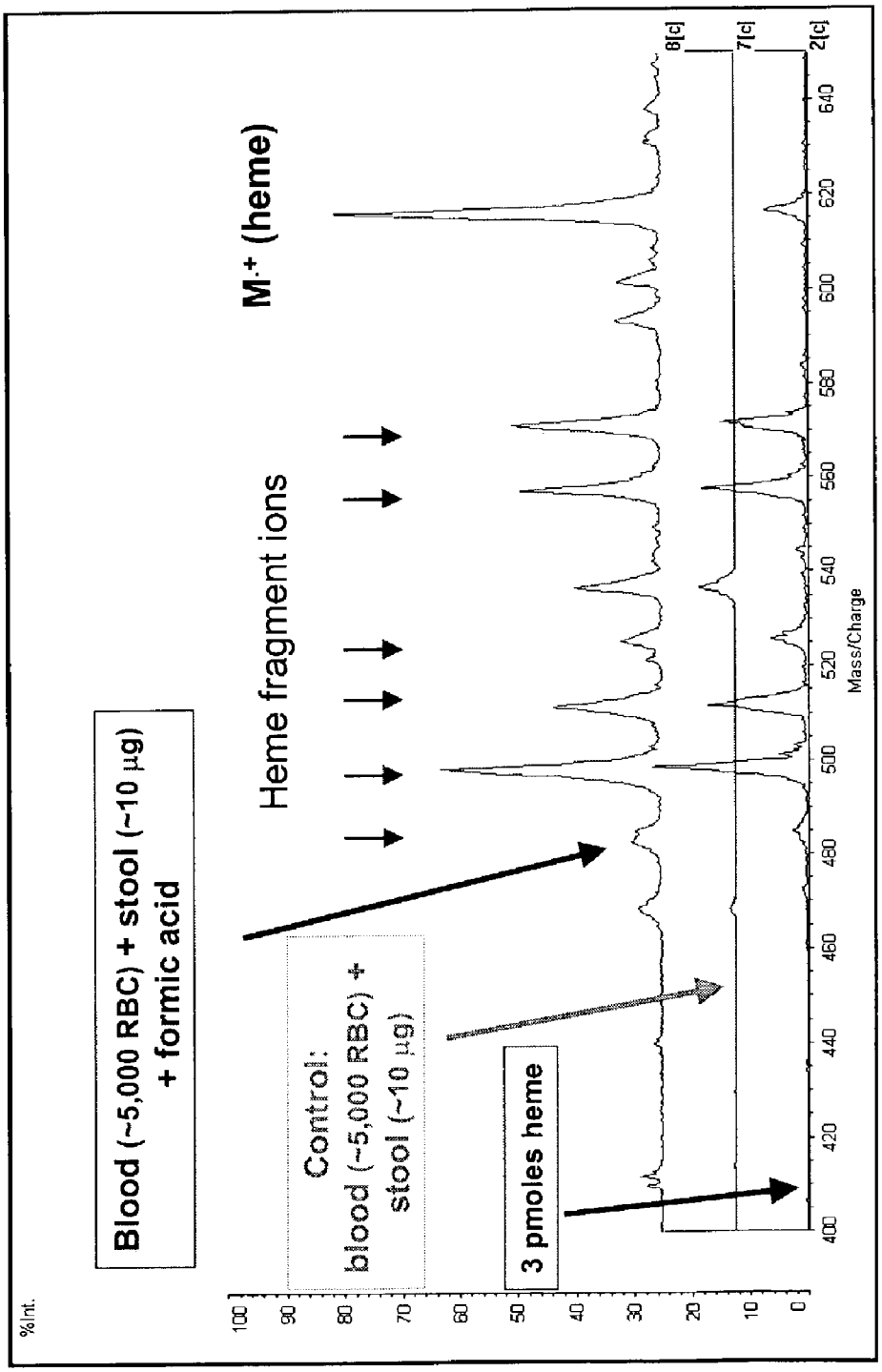
FIG. 2 is a collection of LD mass spectra that show the presence of characteristic heme ion signals in a stool sample treated with acid.

The spectra in FIG. 2 show that occult blood can be detected in stool using LD MS. The first (bottom) spectrum is of a first control sample of three (3) picomoles of unbound heme standard (Sigma Chemical Co) in ammonium hydroxide solution, deposited on a support, dried and analyzed. As expected, characteristic peaks for heme and its fragment ions are clearly identifiable. The second (middle) spectrum is of a second control sample containing whole blood having about 5,000 red blood cells (RBCs) plus about 10 micrograms of stool in a buffered solution of phosphate buffer saline (PBS). The corresponding spectrum does not display any peaks corresponding to heme because the second control sample was not treated with acid, therefor it had no unbound heme. Finally, the top spectrum is that of the test sample. To form the test sample, a thin layer of about 0.4 microliters of a mixture of whole blood plus about 10 micrograms of stool in a buffered solution of PBS was deposited on a support and it was dried. About 0.4 microliters of concentrated formic acid was then applied to the deposited sample to hydrolyze heme from hemoglobin. After drying, the test sample was analyzed. The (top) spectrum of the acid-treated test sample displays the characteristic heme molecular and fragment ions that are present in the spectrum of the control heme-containing sample (bottom). Thus, one embodiment of the present method is directed to detecting FOB in a biological sample using LD MS analysis of heme in an acid-treated stool sample. This same method can be used to detect occult blood in other biological samples.

Figure 3:
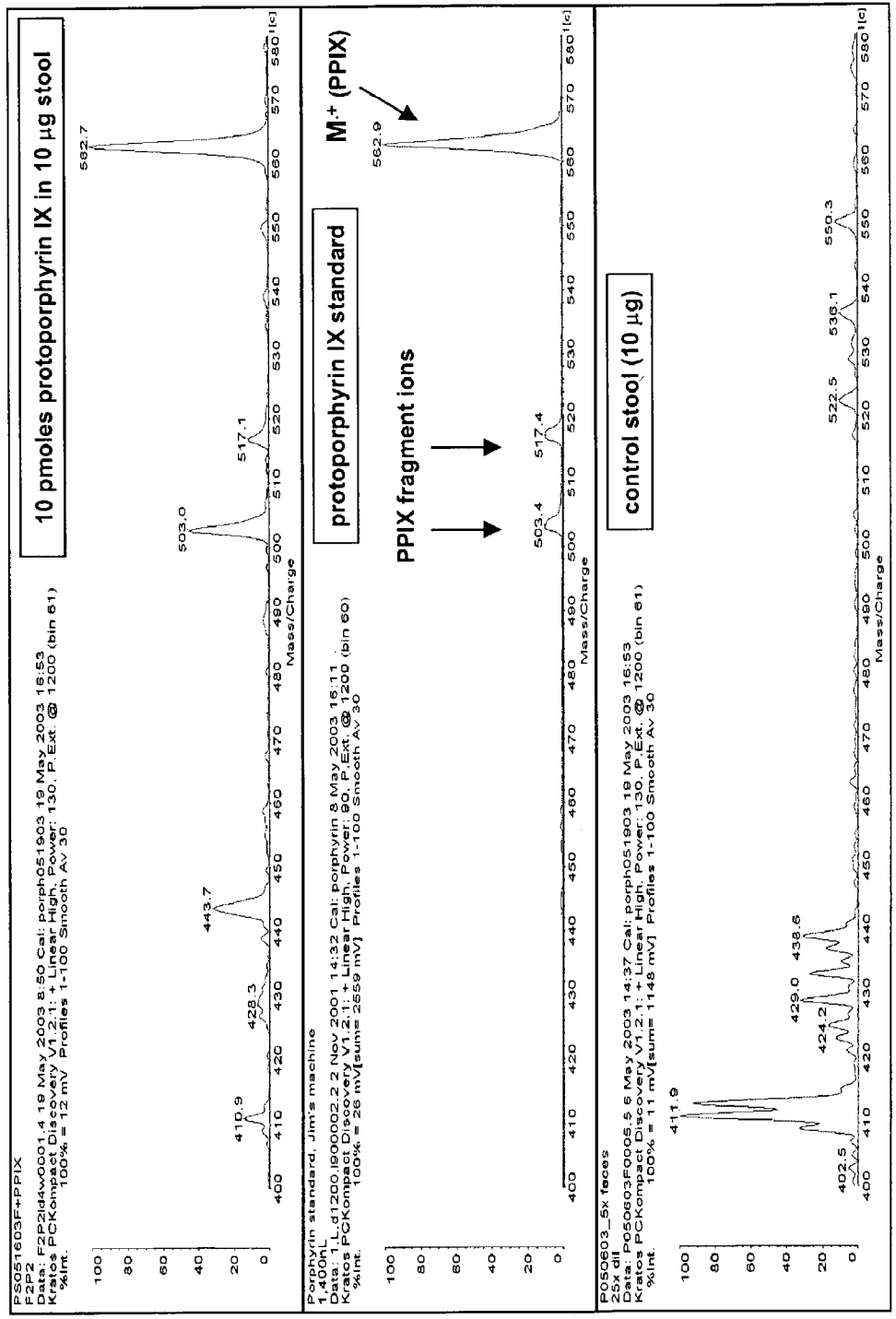
FIG. 3 is a collection of LD mass spectra of unbound PPIX in stool.

FIG. 3 illustrates LD MS spectra of commercial samples of protoporphyrin IX (PPIX) in control and stool samples. PPIX has the composition $C_{34}H_{34}N_4O_4$, $M_{mono}$=562.257, $M_{ave}$=562.667 Da and it was obtained from Sigma Chemical Co. (St Louis, Mo.). PPIX was dissolved in chloroform and 0.3 microliters was deposited on the stainless steel slide for analysis using LD-TOF mass spectrometry. Any solvent known in the art for dissolving PPIX can be used. External calibration in both polarities was performed with CsI cluster ions. The middle spectrum of PPIX standard in chloroform has small peaks for PPIX fragment ions at m/z 503.4 and 517.4, and a large peak at m/z 562.9, corresponding to the PPIX molecular ion (M+). The bottom spectrum is of a control stool sample in buffer without PPIX. As expected, it has no peaks that correspond to PPIX. The top spectrum is of a test sample mixture of dissolved (unbound) PPIX and stool suspended in buffer. To form the test sample, about 0.4 microliters of sample containing 10 picomoles of PPIX and 10 micrograms of stool was deposited on a support, dried and inserted in the instrument. The results in the top spectrum show the characteristic peaks for PPIX at m/z 503.0 and 517.1, and a large peak at m/z 562.7 designated M+ for PPIX. The results show that unbound PPIX can be detected in a biological sample such as stool using LD-MS. Thus another embodiment of the present method is directed to the detection of blood in a biological sample using LD MS to detect PPIX or other porphyrins (such as bilirubin).

If the porphyrin in the biological sample is in a bound form, the sample can be treated with acid to generate unbound porphyrin for analysis. In some cases where porphyrins exist in bound and unbound forms, it may be desirable to compare the level of porphyrin in an untreated sample with the levels in a sample treated with acid to determine the total amount of porphyrin in the sample. For example, the porphyrin bilirubin exists in both a free and a complexed state. U.S. Pat. No. 6,326,208. Bilirubin is an orange-colored or yellowish substance found in bodily fluids such as blood serum, plasma and amniotic fluid. It is formed as a product of the catabolism of hemoglobin. Bilirubin is transported throughout the body in blood serum attached to serum albumin. Bilirubin is conjugated with glucuronic acid in the liver to form the diglucuronide. In its water soluble conjugated glucuronide form, bilirubin enters the biliary system for excretion in the bile. There are two forms of bilirubin found in blood, namely conjugated bilirubin and unconjugated bilirubin. Conjugated bilirubin is water soluble, whereas unconjuated bilirubin is non-water soluble. The embodiments of the present methods can be used to measure unconjugated bilirubin (and other unconjugated porphyrins) in whole blood or another biological sample without acid treatment. Samples with acid treatment can also be analyzed. The difference between the two samples will indicate the amount of conjugated and unconjugated bilirubin.

Figure 4:
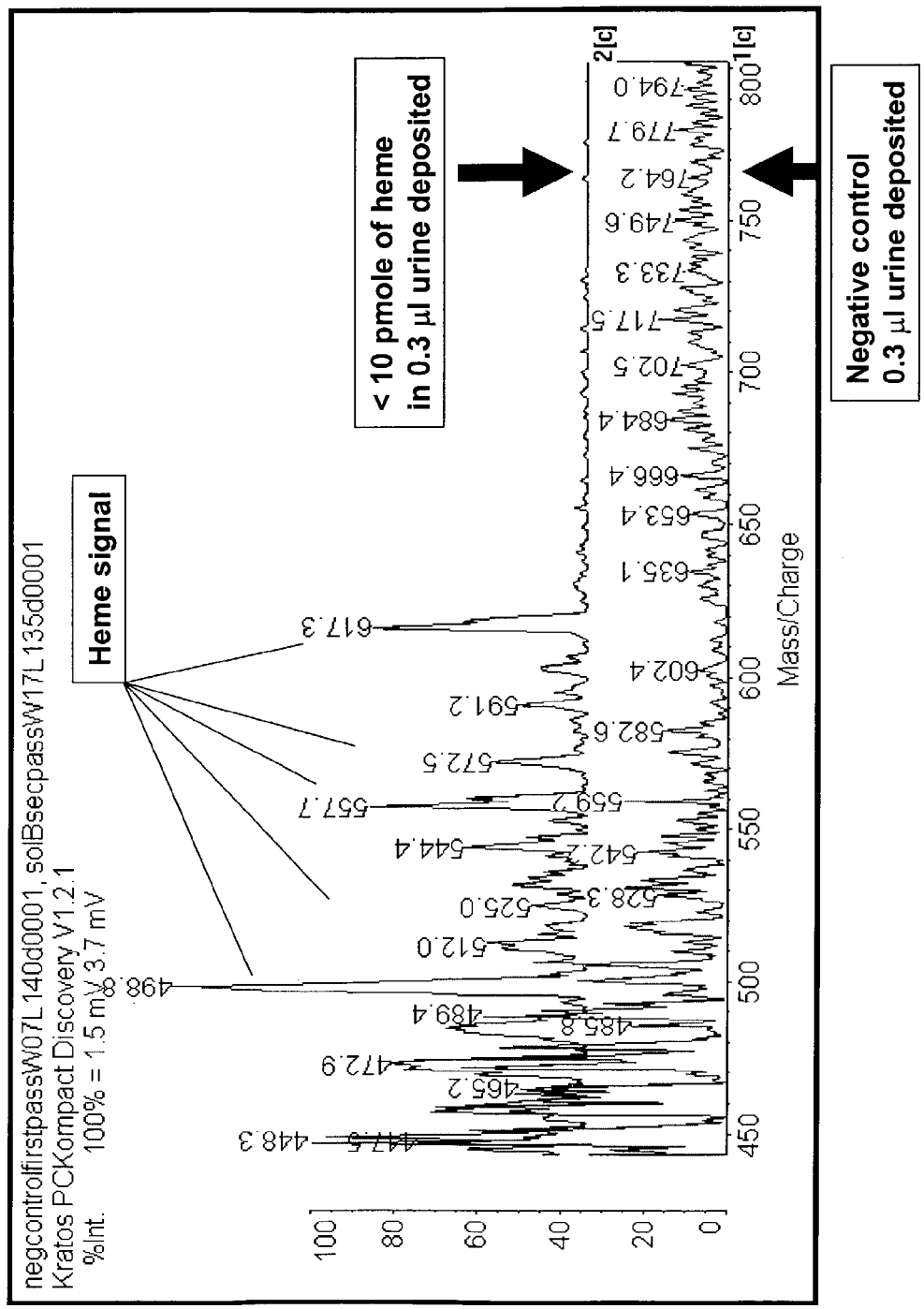
FIG. 4 is a collection of LD mass spectra that show the presence of characteristic heme ion signals in urine sample containing heme standard.

Samples for use in the present methods can be preconcentrated, or the hemoglobin, heme, porphyrins or other metabolites to be analyzed can be extracted or highly purified prior to LD MS analysis. The results reported herein show that no purification steps are necessary, even for FOB. However, further purification steps known in the art can be used where a higher degree of sensitivity is desired. Any method known in the art to clean up, separate and concentrate hemoglobin, heme, hemoglobin metabolic products including PPIX can be used, including, for example, any filtration or chromatography method. Other embodiments of the present method use LD MS to detect and quantify occult blood in urine, as is illustrated in FIG. 4. In these experiments, unbound heme standard was used, therefore there was no need to use an acid on the sample. The bottom spectrum corresponds to a control of 0.3 microliters of urine deposited directly on a support and dried before analysis using LD MS. It does not display peaks corresponding to heme or its fragment ions. The top spectrum is of a test sample mixture of fresh urine with heme standard solution. About 0.3 microliters of urine containing 10 picomoles of heme standard is deposited and dried on a support before LD MS analysis. In sharp contrast to the control, the top spectrum of the test sample shows the characteristic peaks for heme and its fragment ions, indicated by arrows in the figure. This shows that LD MS can detect occult blood in urine by the presence of heme in the sample. Since heme in urine is in a bound state, the sample can be mixed with or treated with acid before LD MS analysis.

In yet another embodiment, signal processing is used to reject background clutter to increase the clarity of the heme signal and/or the signal for other porphyrins. To accomplish this, an individual laser shot mass spectrum is run through a matched filter for heme or other porphyrins to produce a filtered average that is more readily interpreted.

It is emphasized that the LD methods reported in the literature for detecting hemoglobin in whole blood do not include the detection of heme or other hemoglobin metabolites in a biological sample. The present embodiments have several distinct advantages over measuring hemoglobin using MALDI. LD MS has higher sensitivity and specificity for heme and other porphyrins like PPIX in complex biological samples. While MALDI generates predominantly biomarker molecular ions, the presence of specific heme or other porphyrin-specific fragments in LD MS spectra allows their unambiguous identification. Further, many of the common matrixes used in MALDI produce background (cluster) ions in the mass range of interest for detection of heme and other porphyrins.

To summarize, the present LDMS methods require no purification steps to detect heme, hemoglobin alpha and beta polypeptide chains and other porphyrins in biological samples even when used for detection of fecal occult blood (FOBT). Bound heme and bound porphyrins in a biological sample can be converted to unbound forms by a simple acid treatment. As was mentioned earlier, heme in the stomach is converted by hydrochloric acid to unbound protoporphyrin IX (PPIX). PPIX can be identified and quantified directly by LD MS analysis according to various embodiments of the methods of the present invention. The presence of PPIX in stool signifies blood loss in the upper gastrointestinal (GI) tract. Thus the methods of the present invention that use LD MS to unambiguously detect and quantify PPIX and heme, have considerable clinical value. None of the other tests known in the art enable the direct detection and quantification of PPIX.

1.2 MALDI Detection and Quantification of Occult Blood

Some embodiments of the present invention detect occult blood in a biological sample using MALDI by the presence of hemoglobin alpha ($\alpha$)- and beta ($\beta$)-chains. FIG. 5. Alpha-cyano 4-hydroxycinamic acid was used as a matrix for MALDI analysis of all samples; specifically a saturated solution in acetonitrile/water, 50/50 by volume. Other suitable MALDI matrixes or solvents, known in the art can be determined using routine experimentation. The top spectrum in FIG. 5 is of a first control sample of stool that shows no ions in the m/z range from 6,000 to 20,000. The middle spectrum is of a second control sample that contains a known amount of blood (no stool) that has ion peaks designated M++$\alpha$, M+$\alpha$ and M+$\beta$ at about m/z 7,800, 15,250 and 16,000, respectively. The bottom spectrum is of a test sample that contains a known amount blood mixed with a stool suspension. The stool suspension contains 10 micrograms of stool and 5000 RBC. About 0.4 microliters of this suspension is deposited on a support. After it is dry, about 0.4 microliters of matrix solution is applied. The sample is then analyzed using MALDI. The spectrum of the test sample (bottom) has ion peaks for hemoglobin polypeptide chains designated M++$\alpha$, M+$\alpha$ and M+$\beta$, at about m/z 7,800, 15,250 and 16,000, respectively. More intense doubly-charged ions are detected from the alpha-chain. Both singly-and doubly-charged ions form clusters with the matrix molecules (a known property of the alpha-cyano-4-hydroxycinamic acid matrix used—hence the double and triple peaks). These spectra show that MALDI mass spectrometry can be used to detect fecal occult blood by detecting the hemoglobin alpha- and beta-chains with no purification steps. MALDI can be used to detect blood in other biological samples as well.

2.0 Experimental Setup

In the experiments the sample was deposited in a 2×1 mm$^2$ well on a stainless steel sample holder for LD-TOF mass spectrometry analysis. Samples were allowed to dry in air prior to introduction into the instrument. External calibration in both polarities was performed with CsI cluster ions as is described in the art.

Positive and negative ion mass spectra were obtained on a Kompact MALDI 4 (Kratos Analytical Instruments, Chestnut Ridge, N.Y.) time-of-flight instrument at (+/−) 20 kV nominal accelerating voltage. An N$_2$ laser ("VSL-337ND" Laser Science Inc., MA, provided with the instrument) had an estimated fluence of 10 mJ/cm$^2$ (ml per square centimeter) before attenuation (0.2 mJ average energy/pulse at 337 nm (nanometer) laser wavelength, pulse duration 4 ns). Pulsed ion (delayed) extraction was optimized for ion focusing and transmission at m/z 1200 for LD or m/z 15000 for MALDI. Spectra were acquired in linear and reflectron modes. Unless otherwise stated, each spectrum was the average of 100 consecutive laser shot traces, with the beam incrementally moved ("rastered linearly") after each laser shot across the entire sample well. A beam density of p130 (instrument setting) was optimal for detecting heme and PPIX.

The LD-TOF mass spectra of heme samples, performed in positive ion and linear mode had an intensity normalized to 289 mV and in negative ion and linear mode had an intensity normalized to 21 mV. Various mass analyzers are used in various embodiments for LD mass spectrometry, e.g., magnetic sector/magnetic deflection instruments, single or triple quadrupole mode (mass spectrometry/mass spectrometry), Fourier transform and time-of-flight (TOF) configurations that are known in the art of mass spectrometry.

In both positive and negative ion modes, intense molecular ion peaks are observed, with masses corresponding to the heme or porphyrin radical ion species $M^{+\cdot}$ or $M^{-\cdot}$, respectively No doubly- or triply charged ions from heme or porphyrins are detected by LD MS in either positive or negative ionization mode. Under otherwise identical LD-TOF instrumental conditions, the signal intensity in the positive ion mode is about an order of magnitude higher, compared to negative ions, for both heme and PPIX. While the mass resolution at m/z 600 in reflectron mode is a factor of 4 higher (1200 full width at half maximum—FWHM), compared to linear mode (300 FWHM), the signal in linear mode is a factor of 10 to 100 more intense.

Any material compatible with the mass spectrometer can be used to introduce the sample into the mass spectrometer for analysis, including glass, paper, metal and plastic, and their chemical modifications.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for detecting porphyrin in a biological sample obtained from an animal using laser desorption mass spectrometry, comprising the steps of:
   a. obtaining a biological sample from the animal,
   b. depositing the biological sample on a support without purifying the sample,
   c. treating the biological sample with an acid for converting bound porphyrin to unbound porphyrin either before or after step b,
   d. inserting the support into a laser desorption mass spectrometer,
   e. obtaining a mass spectrum of the biological sample,
   f. determining whether the mass spectrum shows a mass/charge signature of the unbound porphyrin, and g. if it is determined that the mass spectrum shows the mass/charge signature of the unbound porphyrin, then concluding that the biological sample contains porphyrin, wherein the porphyrin is bilirubin.

2. A method for detecting porphyrin in a biological sample obtained from an animal using laser desorption mass spectrometry, comprising the steps of:
   a. obtaining a biological sample from the animal,
   b. depositing the biological sample on a support without purifying the sample,
   c. treating the biological sample with an acid for converting bound porphyrin to unbound porphyrin either before or after step b,
   d. inserting the support into a laser desorption mass spectrometer,
   e. obtaining a mass spectrum of the biological sample,
   f. determining whether the mass spectrum shows a mass/charge signature of the unbound porphyrin, and
   g. if it is determined that the mass spectrum shows the mass/charge signature of the unbound porphyrin, then concluding that the biological sample contains porphyrin, wherein the porphyrin is biliverdin.

3. A method for detecting blood in a biological sample obtained from an animal using matrix assisted laser desorption mass spectrometry, comprising:
   a. obtaining a biological sample that is not whole blood from the animal,
   b. preparing a test sample from the biological sample by combining the biological sample with an acid and a matrix,
   c. depositing the test sample on a support without purifying the sample,
   d. inserting the support into a mass spectrometer,
   e. Obtaining a mass spectrum of the test sample,
   f. determining whether the mass spectrum shows a mass/charge signature of hemoglobin polypeptide chains, and
   g. if it is determined that the mass spectrum shows the mass/charge signature of hemoglobin polypeptide chains, then concluding that the test sample contains blood.

4. The method of claim 3, wherein the hemoglobin peptides are alpha-polypeptides.

5. The method of claim 3, wherein the hemoglobin peptides are beta-polypeptides.

6. The method of claim 3, wherein the biological sample in step a is feces.

7. The method of claim 3, wherein the biological sample in step a is urine.

8. The method of claim 3, wherein the matrix is alpha-cyano 4-hydroxycinamic acid.

* * * * *